(12) United States Patent
Sklar

(10) Patent No.: US 10,743,954 B2
(45) Date of Patent: Aug. 18, 2020

(54) THERAPEUTIC GARMENT FOR TREATMENT OF OVER-SHUNTING HEADACHES AND METHOD FOR USE OF SAME

(71) Applicant: Frederick H. Sklar, Waxahachie, TX (US)

(72) Inventor: Frederick H. Sklar, Waxahachie, TX (US)

(*) Notice: Subject to any disclaimer, the term of this patent is extended or adjusted under 35 U.S.C. 154(b) by 203 days.

(21) Appl. No.: 13/767,651

(22) Filed: Feb. 14, 2013

(65) Prior Publication Data

US 2013/0211444 A1  Aug. 15, 2013

Related U.S. Application Data

(60) Provisional application No. 61/598,707, filed on Feb. 14, 2012.

(51) Int. Cl.
*A61B 34/00* (2016.01)
*A61F 5/02* (2006.01)
*A61F 5/03* (2006.01)

(52) U.S. Cl.
CPC .......... *A61B 34/70* (2016.02); *A61F 5/02* (2013.01); *A61F 5/03* (2013.01)

(58) Field of Classification Search
CPC .......... A61F 5/028; A61F 13/148; A61F 5/02; A41D 2400/38; A41C 1/003
USPC ........ 2/404, 407; 450/95, 96, 100–106, 113, 450/116–119, 134–138, 141, 142, 154, 450/155; 602/67–71; 606/201
See application file for complete search history.

(56) References Cited

U.S. PATENT DOCUMENTS

| | | | |
|---|---|---|---|
| 5,205,815 A * | 4/1993 | Saunders | 602/19 |
| 6,463,765 B2 | 10/2002 | Blakely | |
| 7,024,892 B2 | 4/2006 | Blakely | |
| 8,257,289 B2 | 9/2012 | Vess | |
| 8,568,195 B1 * | 10/2013 | Schindler | A41C 1/06 450/30 |

(Continued)

FOREIGN PATENT DOCUMENTS

EP    2316521    5/2011

OTHER PUBLICATIONS

Farlex Partner Medical Dictionary. S.v. "costal margin." Retrieved Jan. 11, 2016 from http://medical-dictionary.thefreedictionary.com/costal+margin.*

(Continued)

*Primary Examiner* — Thomas McEvoy
(74) *Attorney, Agent, or Firm* — Scott Griggs; Griggs Bergen LLP

(57) ABSTRACT

A therapeutic garment for treatment of over-shunting headaches and method for use of the same are disclosed. In one embodiment, the therapeutic garment includes a waistband and an abdominal portion that extends from the waistband to encircle the abdomen and hips from the groin to the costal margin of a person wearing the therapeutic garment. A binder portion, having open and closed positions, is coincident to the abdominal portion. In the closed position, the binder distends the epidural venous plexus of the person wearing the therapeutic garment. A closure mechanism is configured to selectively alternate the binder between the open and closed positions. The therapeutic garment may further be fashioned into a brief, a tank top, or include leg extensions.

5 Claims, 2 Drawing Sheets

(56) References Cited

U.S. PATENT DOCUMENTS

| | | | |
|---|---|---|---|
| 2009/0138064 A1* | 5/2009 | Horn | 607/108 |
| 2009/0192432 A1* | 7/2009 | Frazer | 602/61 |
| 2011/0054373 A1* | 3/2011 | Reiley | A61B 6/04 |
| | | | 602/19 |
| 2013/0095730 A1* | 4/2013 | Jensen | A41C 1/003 |
| | | | 450/95 |

OTHER PUBLICATIONS

Sklar FH, Nagy L, Robertson BD, The Use of Abdominal Binders to Treat Over-Shunting Headaches, J Neurosurg Pediatr, Jun. 2012;9(6):615-620, doi: 10.3171/2012.2.PEDS11146, Children's Medical Center, Dallas, Texas, USA.
International Searching Authority, International Search Report, PCT/US 13/26207, dated May 3, 2013.

* cited by examiner

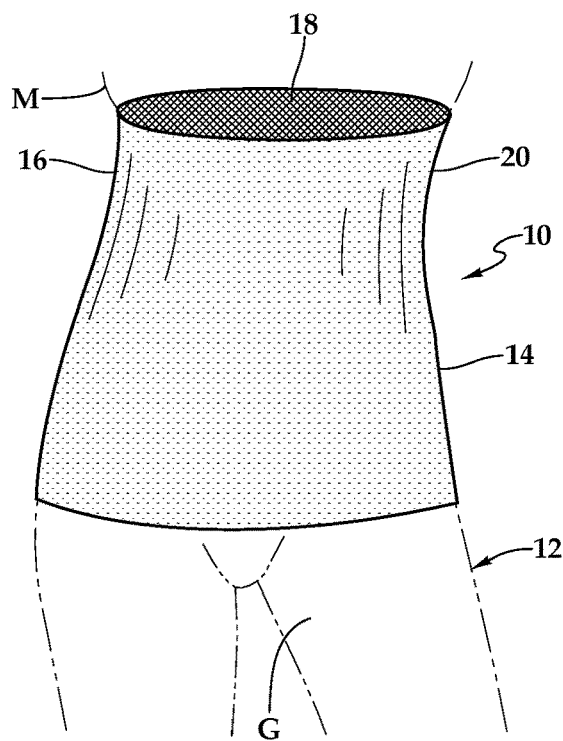
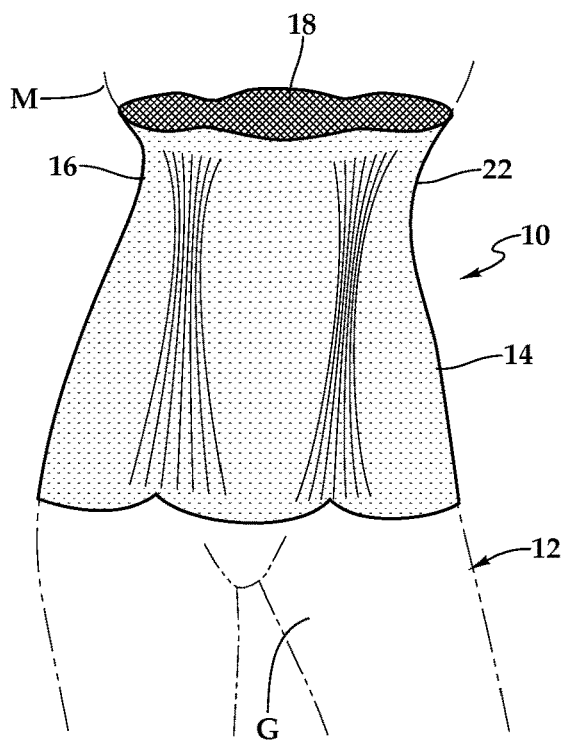
Fig.1A
Fig.1B
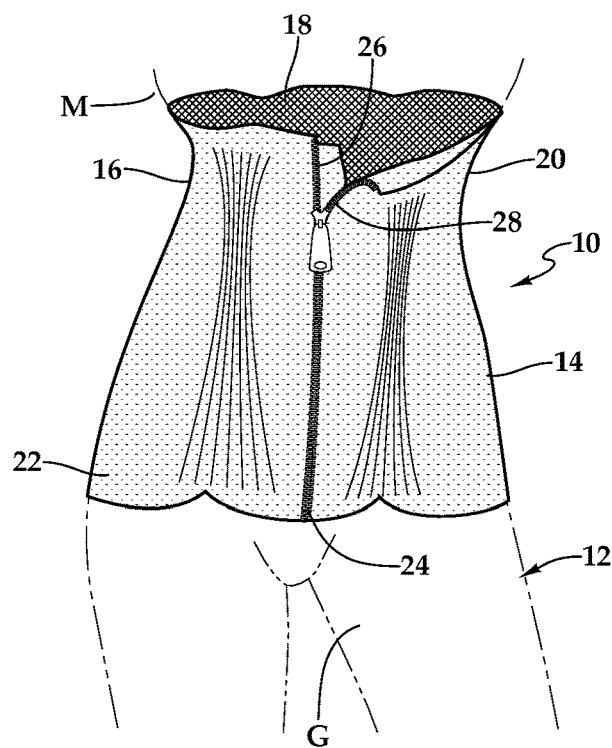
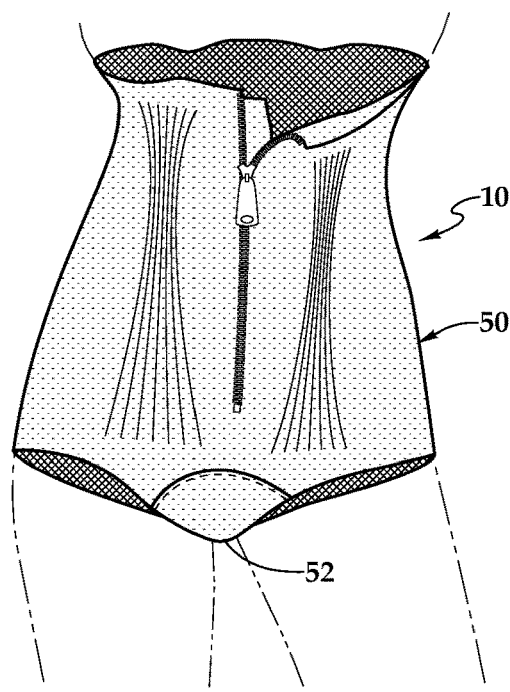
Fig.2
Fig.3

THERAPEUTIC GARMENT FOR TREATMENT OF OVER-SHUNTING HEADACHES AND METHOD FOR USE OF SAME

PRIORITY STATEMENT AND CROSS-REFERENCE TO RELATED APPLICATION

This application claims priority from U.S. Patent Application No. 61/598,707, entitled "Garments for Treatment of Over-shunting Headaches and Method for Use of Same," and filed on Feb. 14, 2012 in the name of Fredrick H. Sklar; which is hereby incorporated by reference for all purposes.

TECHNICAL FIELD OF THE INVENTION

This invention relates, in general, to the field of medical devices and, in particular, a therapeutic garment, and a method for use of same, for the treatment of over-shunting headaches in certain neurosurgical patients who are symptomatic of over-shunting and other neurosurgical conditions that cause intercranial hypotension.

BACKGROUND OF THE INVENTION

In adult and pediatric neurosurgery, cerebrospinal fluid (CSF) shunts are commonly used to treat hydrocephalus, arachnoid cysts, benign intracranial hypertension (pseudotumor cerebri), and other neurosurgical conditions characterized by raised intracranial pressure (ICP). Shunt over-drainage of CSF occurs with frequency—some shunts more than others. These patients develop intracranial hypotension, presumably related to the siphoning of CSF from the head when the patient is upright. This condition is referred to as over-shunting.

Children and adults with over-shunting frequently experience headaches. In a recent retrospective clinical review, 23% of shunted patients had headaches that were thought by the neurosurgeon to be the result of over-shunting on the basis of their clinical pictures. In addition, there are patients with headaches resulting from intracranial hypotension, due to the escape or over-drainage of CSF as a result of a lumbar puncture (the so-called spinal tap headache), post-operative pseudomeningocele, and chronic CSF leakage (CSF ottorhea and rhinorrhea).

Over-shunting headaches are usually intermittent. They tend to come on later in the day; patients rarely awaken with headache. There is frequently a postural component: laying down helps the headache. The ventricles are usually small on MRI or CT scan. Intracranial pressure is low, as indicated by introducing a needle into the shunt (the so-called shunt tap). A need exists for a solution to over-shunting headaches in particular patients.

SUMMARY OF THE INVENTION

It would be advantageous to achieve garments for treatment of over-shunting headaches and a method for use of the same. It would also be desirable to enable aphysiological-medical based solution that would be non-encumbering and allow patients to use the solution while going about a daily routine. To better address one or more of these concerns, in one aspect of the invention, therapeutic garments for treatment of over-shunting headaches and a method for use of the same are disclosed. In one embodiment, the therapeutic garment includes a waistband and an abdominal portion that extends from the waistband to encircle the abdomen and hips from the groin to the costal margin of a person wearing the therapeutic garment.

A binder portion, having open and closed positions, is coincident to the abdominal portion. In the closed position, the binder distends the epidural venous plexus of the person wearing the therapeutic garment. A closure mechanism is configured to selectively alternate the binder between the open and closed positions. The therapeutic garment may further be fashioned into a brief, a tank top, or include leg extensions.

In patients, the therapeutic garment presented herein fulfills a need that exists in patients suffering from over-shunting headaches. Patients wearing the therapeutic garment on the abdomen (referred to as an abdominal binder, originally designed for patients with general surgical conditions) twenty four (24) hours a day for four to six (4-6) weeks have fewer headaches. Approximately 87% of patients experience marked improvement or complete relief of over-shunting headaches with the use of the therapeutic garment. Moreover, 71% of patients who have a favorable response to the use of the therapeutic garment experience complete relief of headache. Further, the headache relief usually persists after the therapeutic garment is removed. The majority of patients (59%) start having headache again, but usually after a year or more. Recurrent headache responds to reuse of the therapeutic binder in 79% of patients. These and other aspects of the invention will be apparent from and elucidated with reference to the embodiments described hereinafter.

BRIEF DESCRIPTION OF THE DRAWINGS

For a more complete understanding of the features and advantages of the present invention, reference is now made to the detailed description of the invention along with the accompanying figures in which corresponding numerals in the different figures refer to corresponding parts and in which:

FIG. 1A is a front schematic diagram of one embodiment of a therapeutic garment for treatment of over-shunting headaches in an open position being worn by a person;

FIG. 1B is a front schematic diagram of the therapeutic garment of FIG. 1A in a closed position being worn by the person;

FIG. 2 is a front perspective diagram of the therapeutic garment in FIGS. 1A and 1B;

FIG. 3 is a front perspective diagram of another embodiment, labeled a brief embodiment, of a therapeutic garment for treatment of over-shunting headaches;

DETAILED DESCRIPTION OF THE INVENTION

Figure 4:
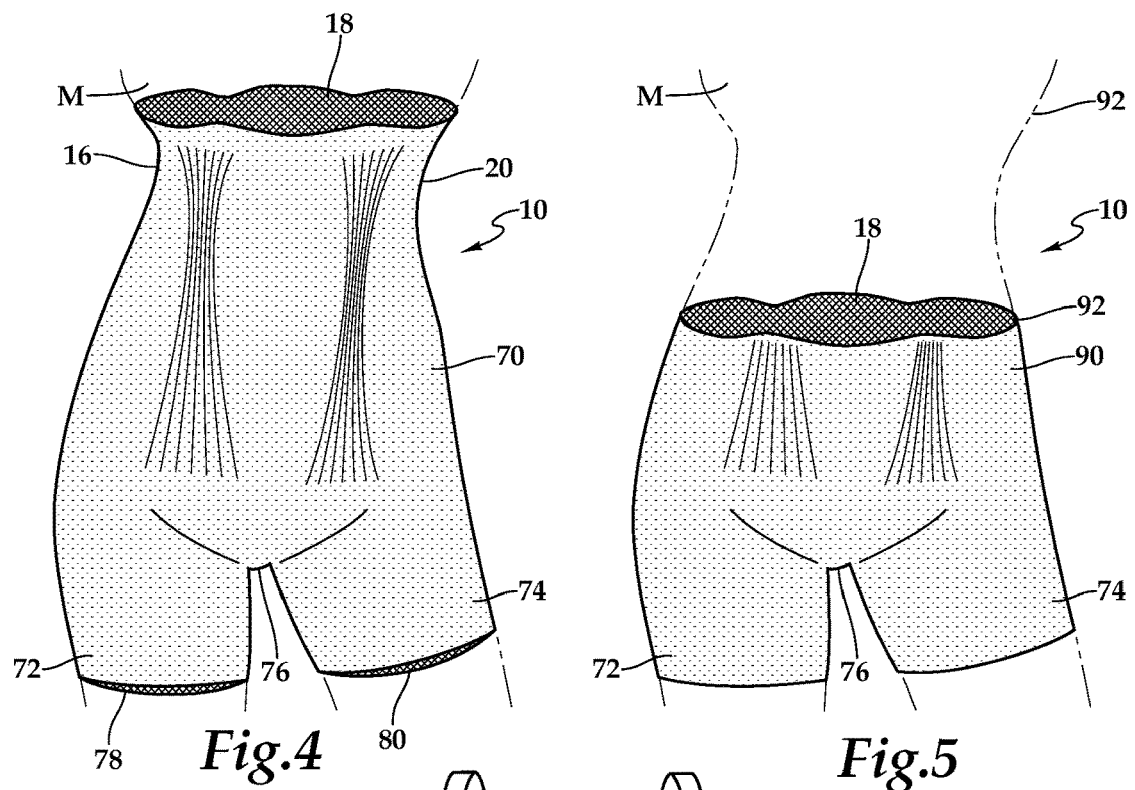
FIG. 4 is a front perspective diagram of a further embodiment, a leg extension embodiment, of a therapeutic garment for treatment of over-shunting headaches.

While the making and using of various embodiments of the present invention are discussed in detail below, it should be appreciated that the present invention provides many applicable inventive concepts, which can be embodied in a wide variety of specific contexts. The specific embodiments discussed herein are merely illustrative of specific ways to make and use the invention, and do not delimit the scope of the present invention.

Referring initially to FIGS. 1A, 1B and 2, therein is depicted a therapeutic garment for treatment of over-shunting headaches that is schematically illustrated and generally designated 10, being worn in FIGS. 1A and 1B by a person 12. The therapeutic garment 10 includes a waistband 14 and an abdominal portion 16 that extends from the waistband 14. The abdominal portion 16 and the waistband 14 together encircle the abdomen and hips from the groin G to the costal margin M of the person 12 wearing the therapeutic garment 10. A binder portion 18 is coincident to the abdominal portion 16. In one embodiment, the abdominal portion 16 and binder portion 18 are integral and integrally formed and thereby define an interior for contact with the person and an exterior. The abdominal portion 16 and binder portion 18 may be formed of an elastic, latex-free material. Alternatively, Lycra yarn, spandex yarn nylon yarn, or a plane-knit based fabric may be utilized.

As shown, the binder portion 18 has open and closed positions, which are labeled as open position 20 and closed position 22. The binder portion 18 in the closed position 22 is configured to distend the epidural venous plexus of the person 12 wearing the therapeutic garment. A closure mechanism 24 is configured to selectively alternate the binder between the open and closed positions 20, 22. The close mechanism 24 may be a zipper, Velcro fastener, or other closing mechanism. The closure site may be backed by a narrow flap of soft, non-elastic material for patient comfort.

As illustrated, a vertical opening 26 with a flap 28 may extend along the garment axially to provide a location for the closure mechanism 24. As an alternative or addition, drawcord pulley laces may be included to further facilitate application of the therapeutic garment 10. Such an alternative or addition may be particularly useful with obese teenagers or adults with a pendulous abdomen. Further, although not shown, a print or design may be added to the therapeutic garment 10.

In this embodiment, the neurosurgical abdominal binders or therapeutic garments are tailored into a gentle hour-glass shape to facilitate a good fit at the waist. The therapeutic garments are manufactured in multiple sizes to extend from the patient's costal margins down to the groin. Thus, the vertical height of the therapeutic garment is an important determination of size, ranging from 8" to 16" inches (approximately 20 to 40 centimeters), and can be made available at various intermediate increments. This system will allow appropriate sizing of patients, ranging from small infants to tall adults. Multiple tubular circumferences based on body habitus will be available for each vertical height measurement. In addition, longer circumferential length binders are also available to accommodate full sized adult patients.

Figure 5:
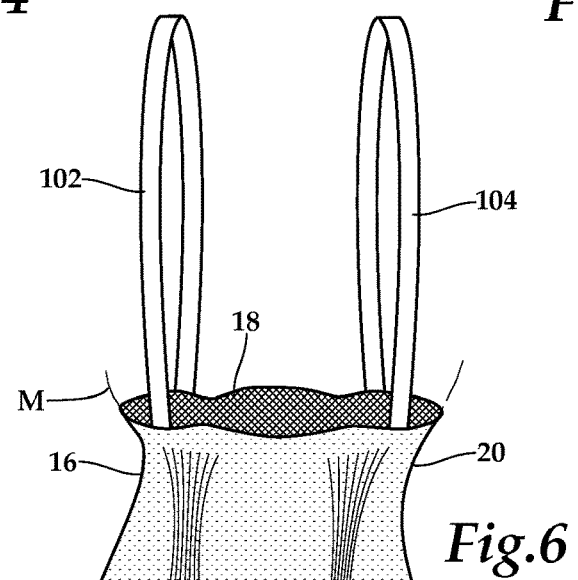
FIG. 5 is a front perspective diagram of a still further embodiment, a leg extension with reduced height embodiment, of a therapeutic garment for treatment of over-shunting headaches.

Referring to FIG. 3, one embodiment of the therapeutic garment 10 for treatment of over-shunting headaches is depicted, wherein the therapeutic garment 10 is incorporated into a brief 50 having a crotch 52, which may include appropriate access openings. Referring to FIG. 4, another embodiment of the therapeutic garment 10 is shown, a leg extension embodiment 70. Leg portions 72, 74 extend down from the abdominal portion to define a crotch portion 76 therebetween. Leg binder portions 78, 80 are coincident with the leg portions 72, 74. The leg binder portions 78, 80 are configured to exert pressure on the supra-pubic and inguinal ligament groin areas of the person wearing the therapeutic garment. FIG. 5 depicts a further variation wherein a leg extension embodiment 90 includes a reduced height 92. The abdominal portion extends from the waistband to encircle the abdomen and hips from the groin to an interior costal margin location of a person wearing the therapeutic garment. With respect to the leg extensions, extension of the elastic fabric of the brief down onto the thighs may be desirable for additional compression of the femoral veins at the inguinal ligaments. This may improve binder function in cases of persistent headache despite the use of the standard neurosurgical binder or binders with briefs. Girls and women may prefer this option for fashion considerations.

Figure 6:
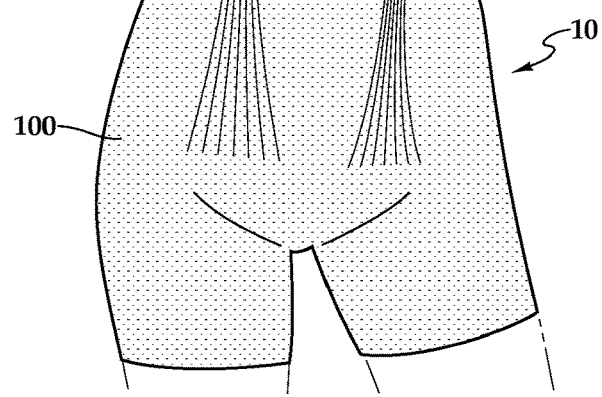
FIG. 6 is a front perspective diagram of an additional embodiment, a tank top embodiment, of a therapeutic garment for treatment of over-shunting headaches.

FIG. 6 is a still further embodiment of the therapeutic garment, wherein the therapeutic garment is incorporated into a tank top 100 having shoulder straps 102, 104. This embodiment will allow maximal physical activity without dislodging binder placement. The patient or person would step into the therapeutic garment at the neck opening and pull the top of the elastic component up to the costal margins. The shoulder straps 102, 104 are then slipped into place. Fabric above the costal margin and that of the shoulder straps do not have to be elastic.

As described herein, therapeutic garments have been developed that exert pressure on the abdomens and groins of children and adult patients with headaches related to over-shunting or other causes of intracranial hypotension. These garments act as neurosurgical abdominal binder and the described spectrum of therapeutic garments includes, but is not limited to a unisex abdominal binder, a binder incorporated into a fitted, elastic brief, a binder-brief combination with over-the-shoulder support, and binder-briefs with leg extensions. In addition, the garments can be designed to be appealing for male or female usage, respectively; to be appealing to specific age groups; and to provide an effective fit over a spectrum of body shapes.

With respect to physiology, intracranial pulse pressures increase with the level of ICP. This is a feature of physiology. In hydrocephalus, this pulse pressure-ICP relationship is exaggerated and the intracranial pulse pressure is abnormally increased. Using CSF withdrawals, it has been shown that reducing pressures below the physiologic baseline will result in marked augmentation of the intracranial pulse pressure-not unlike the pulse pressure increase that is seen at high pressures. Normally, the pressure pulsations of the arteries at the base of the brain displace the CSF of the basal cisterns down the clivus into the spine with each cardiac systole. This can be appreciated on gated CSF studies with an MRI technique. Studying patients undergoing myelography, it has been demonstrated that breathing 5% carbon dioxide causes the spinal sac to enlarge.

On the other hand, hyperventilation causes the brain volume to decrease, and the spinal sac gets smaller as CSF moves back into the head. The spinal epidural veins are in free communication with the large veins of the chest and abdomen, and these epidural veins likely get smaller or enlarge to accommodate CSF movement into and out of the spine during systole and diastole, respectively. In other words, the spinal epidural veins may serve as a shock absorber, since epidural blood can be displaced during systole into the great veins of the chest and abdomen with each bolus of CSF displaced from the head into the spine. In diastole, CSF flow changes direction and moves out of the spine back towards the Circle of Willis. This is a physiologic process.

However, with over-shunting, the volume of CSF is reduced, not only in the ventricles, but also in the cisterns at the base of the brain. It is suggested that the reduced volume of CSF in the basal cisterns cannot effectively transmit the arterial pressure pulsations into the spine where reciprocal pulsatile changes in epidural venous blood can dampen these arterial pulsations. The intracranial pulse pressures become augmented, and the patient may experience adverse symptoms (HA) or signs (VI nerve palsy). It is suggested that the therapeutic garment possibly functions to compress the pelvic veins, which are in free communication with the epidural venous plexus. It is hypothesized that the therapeutic garment distends the epidural venous plexus so that it can function better as a shock absorber; more venous blood can be transiently displaced out of the spine with each systole. The result is a reduction of intracranial pulsations and improvement in signs and symptoms. The therapeutic garment as recited in claim 1, further comprising a crotch portion coupled to the abdominal portion to define a brief.

While this invention has been described with reference to illustrative embodiments, this description is not intended to be construed in a limiting sense. Various modifications and combinations of the illustrative embodiments as well as other embodiments of the invention, will be apparent to persons skilled in the art upon reference to the description. It is, therefore, intended that the appended claims encompass any such modifications or embodiments.

What is claimed is:

1. A method for treating over-shunting headaches, the method comprising:
    measuring intracranial pulsations in a patient experiencing over-shunting headaches;
    tailoring a therapeutic garment for the patient experiencing over-shunting headaches;
    providing the therapeutic garment for the patient, the therapeutic garment including:
        a tailored waistband;
        a tailored abdominal portion that extends from the tailored waistband, the tailored abdominal portion and the tailored waistband together encircle the abdomen and hips from the groin to the superior costal margin area, and ending thereat, of the patient wearing the therapeutic garment, the superior costal margin area being a lower abdominal border of a front of a rib cage beginning at a superior end of a xiphoid process formed by a costal cartilage, the abdominal portion fully covering the superior costal margin area;
        a tailored binder portion coincident to the tailored abdominal portion, the tailored binder portion having open and closed positions;
        the tailored binder portion in the closed position being configured to distend an epidural venous plexus of the patient wearing the therapeutic garment;
        a closure mechanism configured to selectively alternate the binder between the open and closed positions;
        tailored first and second leg portions extending down from the waistband to define a crotch portion therebetween; and
        tailored first and second leg binder portions coincident with the tailored first and second leg portions, the tailored first and second leg binder portions configured to exert pressure on the supra-pubic and inguinal ligament groin areas of the patient wearing the therapeutic garment;
    placing the therapeutic garment on the patient in the closed position;
    exerting pressure on the abdomen and hips to distend the epidural venous plexus of the patient;
    exerting pressure on the supra-pubic and inguinal ligament groin areas of the patient;
    providing treatment of over-shunting headaches; and
    measuring, after the patient wears the therapeutic garment, intracranial pulsations in the patient experiencing over-shunting headaches.

2. The method as recited in claim 1, further comprising the step of incorporating the therapeutic garment into a tank top.

3. The method as recited in claim 1, further comprising integrating the tailored abdominal portion and the tailored binder portion to be integral.

4. The method as recited in claim 1, further comprising providing the tailored abdominal portion and the tailored binder portion to be formed of an elastic, latex-free material.

5. A method for treating over-shunting headaches, the method comprising:
    measuring intracranial pulsations in a patient experiencing over-shunting headaches;
    tailoring a therapeutic garment for the patient experiencing over-shunting headaches;
    providing the therapeutic garment for the patient, the therapeutic garment including:
        a tailored waistband;
        a tailored abdominal portion that extends from the tailored waistband, the tailored abdominal portion and the tailored waistband together encircle the abdomen and hips from the groin to and through the superior costal margin area, and ending thereat, of the patient, the superior costal margin area being a lower abdominal border of a front of a rib cage beginning at a superior end of a xiphoid process formed by a costal cartilage;
        a tailored binder portion coincident to the tailored abdominal portion, the tailored binder portion having open and closed positions;
        the tailored binder portion in the closed position being configured to distend the epidural venous plexus of the patient;
        a closure mechanism configured to selectively alternate the binder between the open and closed positions;
        tailored first and second leg portions extending down from the tailored waistband to define a crotch portion therebetween; and
        first and second leg binder portions coincident with the first and second leg portions, the first and second leg binder portions configured to exert pressure on the supra-pubic and inguinal ligament groin areas of the patient;
    placing the therapeutic garment on the patient in the closed position;
    exerting pressure via the tailored binder on the abdomen and hips to distend the epidural venous plexus of the patient wearing the therapeutic garment;
    exerting pressure via the tailored first and second leg binder portions on the supra-pubic and inguinal ligament groin areas of the patient;
    providing treatment of over-shunting headaches; and
    measuring, after the patient wears the therapeutic garment, intracranial pulsations in the patient experiencing over-shunting headaches.

* * * * *